United States Patent
Kristen et al.

(10) Patent No.: US 6,420,301 B1
(45) Date of Patent: Jul. 16, 2002

(54) TRANSITION METAL COMPLEXES

(75) Inventors: Marc Oliver Kristen, Limburgerhof; Franz Langhauser, Ruppertsberg; Günther Schweier, Friedelsheim; Helmut Sitzmann, Kaiserslautern; Ralf Krammer, Bad Dürkheim; Dirk Saurenz, Hochspeyer, all of (DE)

(73) Assignee: Basell Polyolefin GmbH, Kehl (DE)

( * ) Notice: Subject to any disclaimer, the term of this patent is extended or adjusted under 35 U.S.C. 154(b) by 0 days.

(21) Appl. No.: 09/719,428

(22) PCT Filed: Jun. 12, 1999

(86) PCT No.: PCT/EP99/04056

§ 371 (c)(1), (2), (4) Date: Dec. 12, 2000

(87) PCT Pub. No.: WO99/65923

PCT Pub. Date: Dec. 23, 1999

(30) Foreign Application Priority Data

Jun. 15, 1998 (DE) .......................................... 198 26 403

(51) Int. Cl.[7] .............................. B01J 31/38; C08F 4/44; C08F 4/16

(52) U.S. Cl. ....................... 502/155; 502/104; 502/117; 502/152; 526/160; 526/161; 526/170; 526/172; 526/943; 526/348.6; 526/351; 526/352; 556/11; 556/53

(58) Field of Search .................... 526/160, 161, 526/170, 172, 943, 348.6, 351, 352; 502/104, 117, 152, 155; 556/11, 53

(56) References Cited

U.S. PATENT DOCUMENTS

| | | |
|---|---|---|
| 5,026,798 A | 6/1991 | Canich |
| 5,096,867 A | 3/1992 | Canich |
| 5,504,169 A | 4/1996 | Canich |
| 5,679,812 A | 10/1997 | Winter |

FOREIGN PATENT DOCUMENTS

| | | |
|---|---|---|
| EP | 336 128 | 10/1989 |
| EP | 0 416 815 A2 * | 3/1991 |
| EP | 416 81115 | 3/1991 |
| EP | 420 436 | 4/1991 |
| EP | 0 420 436 A1 * | 4/1991 |
| EP | 520 732 | 12/1992 |
| WO | 94/00500 | 1/1994 |

OTHER PUBLICATIONS

Okuda et al., Organometallics 1995, 14 789–795.*

Organometallics 1995,14,789–795,Okuda et al.

Organometallics 1997,16, 2879–2885, McKnight et al.

* cited by examiner

Primary Examiner—David W. Wu
Assistant Examiner—R. Harlan
(74) Attorney, Agent, or Firm—Keil & Weinkauf

(57) ABSTRACT

Transition metal complexes of the formula (Ia) or (Ib),

-continued

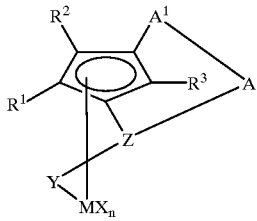

(Ib)

Figure 1:
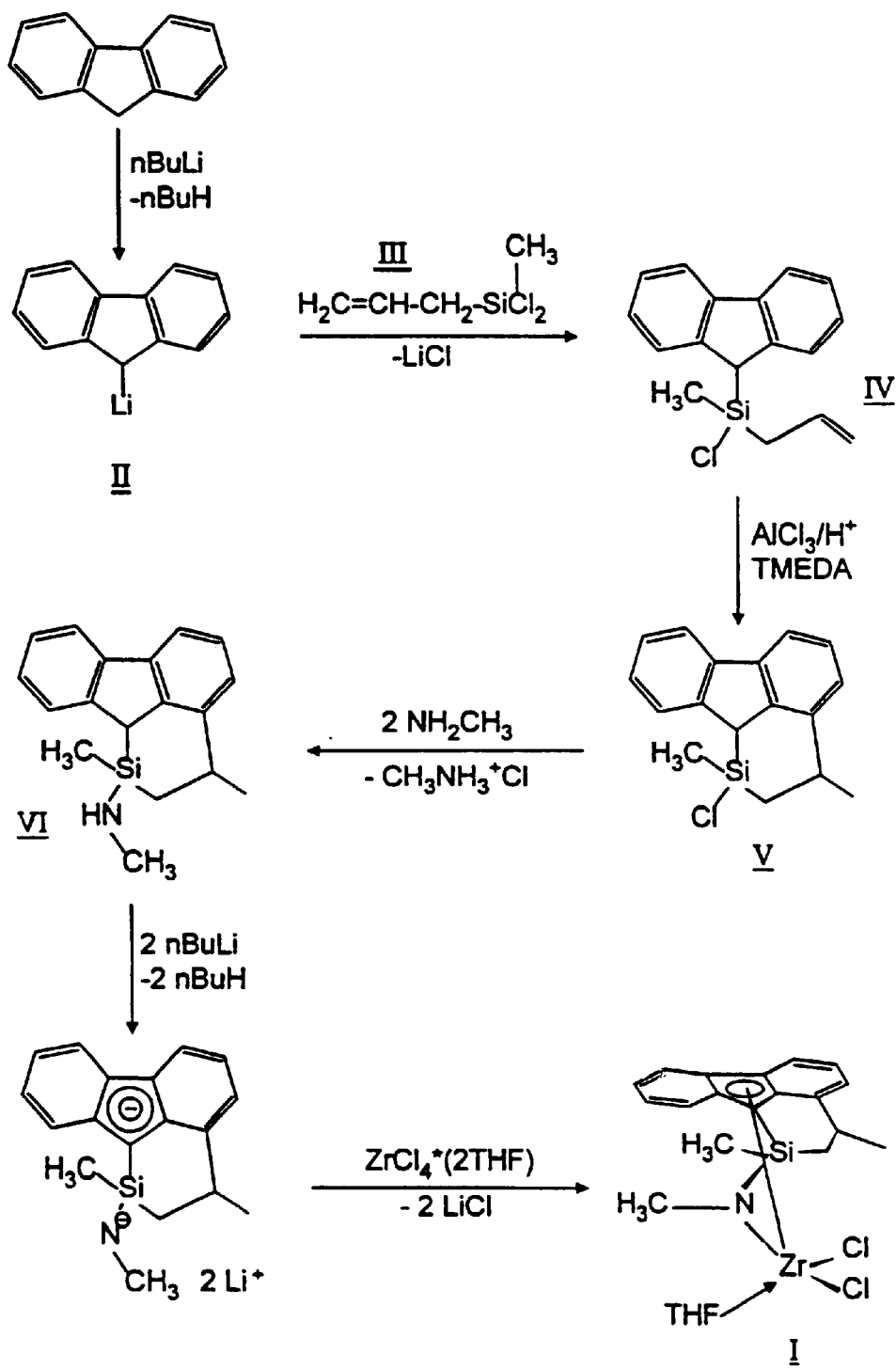

in which the substituents and indices have the following meanings:

M is titanium, zirconium, hafnium, vanadium, niobium or tantalum or an element of the third subgroup of the Periodic Table or of the lanthanoids, X is fluorine, chlorine, bromine, iodine, hydrogen, $C_1$–$C_{10}$-alkyl, $C_6$–$C_{15}$-aryl, alkylaryl having 1 to 10 carbon atoms in the alkyl radical and 6 to 20 carbon atoms in the aryl radical, —$OR^5$ or —$NR^5R^6$, n is 1, 2 or 3, where n is the valency of M minus the number 2, Y is $>NR^7$ or $>PR^7$, Z is a three-way bridge and A and $A^1$ are two-way bridges.

Process for preparing the transition metal complexes, compounds which are used as intermediates for their preparation, the use of the transition metal complexes for polymerizing olefins, processes for polymerizing olefins, homo- or copolymers of ethylene or of propylene with other $C_2$–$C_{12}$-alk-1-enes, their use for preparing films, fibers or moldings and the films, fibers or moldings made of these polymers.

12 Claims, 3 Drawing Sheets

IV

V

TRANSITION METAL COMPLEXES

The present invention relates to transition metal complexes of the formula (Ia) or (Ib),

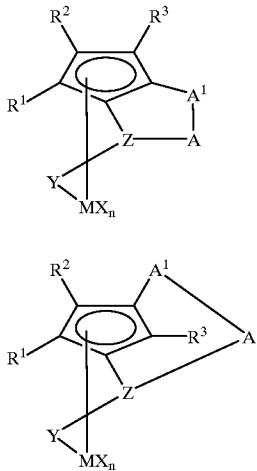

where the substituents and indices have the following meanings:

$R^1$ to $R^3$ are hydrogen, $C_1$–$C_{10}$-alkyl, 5- to 7-membered cycloalkyl, which in turn may be substituted by $C_1$–$C_{10}$-alkyl, are $C_6$–$C_{15}$-aryl or arylalkyl, where the radicals together with adjacent radicals in each case with the linking atoms may form a saturated or unsaturated ring having 5 to 15 carbon atoms, or are $Si(R^4)_3$ where $R^4$ is $C_1$–$C_{10}$-alkyl, $C_3$–$C_{10}$-cycloalkyl or $C_6$–$C_{15}$-aryl, M is titanium, zirconium, hafnium, vanadium, niobium or tantalum or an element of the IIIrd subgroup of the Periodic Table or of the lanthanoids, x is fluorine, chlorine, bromine, iodine, hydrogen, $C_1$–$C_{10}$-alkyl, $C_6$–$C_{15}$-aryl, alkylaryl having 1 to 10 carbon atoms in the alkyl radical and 6 to 20 carbon atoms in the aryl radical, $-OR^5$ or $-NR^5R^6$, n is 1, 2 or 3, where n is the valency of M minus the number 2, where $R^5$ and $R^6$ are $C_1$–$C_{10}$-alkyl, $C_6$–$C_{15}$-aryl, alkylaryl, arylalkyl, fluoroalkyl or fluoroaryl having in each case 1 to 10 carbon atoms in the alkyl radical and 6 to 20 carbon atoms in the aryl radical and the radicals X are identical or different, Y is

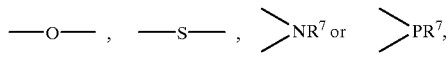

where $R^7$ is $C_1$–$C_{10}$-alkyl, $C_6$–$C_{15}$-aryl, $C_3$–$C_{10}$-cycloalkyl or $C_7$–$C_{18}$-alkylaryl or is $C_1$–$C_{10}$-alkyl, $C_6$–$C_{15}$-aryl, $C_3$–$C_{10}$-cycloalkyl or $C_7$–$C_{18}$-alkylaryl, each of which is mono- or polysubstituted by $Si(R^8)_3$, $SR^8$,

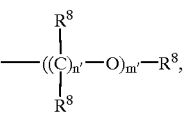

$OSi(R^8)_3$, $N(R^8)_2$, $P(R^8)_2$ or a combination thereof, or is $Si(R^8)_3$ where n' and m' are each 1, 2, 3 or 4 and $R^8$ is hydrogen, $C_1$–$C_{10}$-alkyl, $C_6$–$C_{15}$-aryl, which may in turn be substituted by $C_1$–$C_4$-alkyl groups, or is $C_3$–$C_{10}$-cycloalkyl, where the radicals $R^8$ are identical or different, Z is a three-way bridge and A and $A^1$ are two-way bridges.

Additionally, the invention relates to processes for preparing the transition metal complexes, to compounds which are employed as intermediates for their preparation, to the use of the transition metal complexes for polymerizing olefins, to processes for polymerizing olefins, to homo- or copolymers of ethylene or of propylene with other $C_2$–$C_{12}$-alk-1-enes, to their use for preparing films, fibers or moldings, and to the films, fibers or moldings made from these polymers.

Recently, metallocene catalysts have been used increasingly for polymerizing or copolymerizing ethylene or propylene. In the case of ethylene polymerization, it is frequently desirable to obtain a high content of comonomers such as but-1-ene, hex-1-ene or oct-1-ene in the ethylene copolymers. In the case of propylene polymerization, it is usually attempted to achieve an isotactic structure of the polymer chains. Using metallocene catalysts, these properties can be controlled via the ligand structure.

It is generally assumed that the opening angle between the cyclopentadienyl rings of the metallocene has great influence on the incorporation behavior. A large opening angle can be achieved, for example, by bridging the rings with an $SiMe_2$- or $C_2H_4$-bridge. Such metallocene catalysts are described, for example, in EP-A 336 128. Because of the bridging, these complexes can exist both in racemic and in meso form. The racemic metallocenes are particularly suitable for use in propylene polymerization, since stereoselective catalysts are required here. However, it is a disadvantage of these metallocenes that usually a mixture of racemic and meso form is obtained in the synthesis, from which the meso form has to be removed at high expense.

In other metallocene catalysts, a cyclopentadienyl ring is replaced by a heteroligand, for example an amide group. In these metallocenes, the amide group is linked covalently via a bridge (for example $SiMe_2$) with the ring system. Compounds of this type are described, for example, in EP-A 416 815 and EP-A 420 436. It is known that metallocene complexes of this type are particularly suitable for incorporating comonomers in the ethylene/α-olefin copolymerization and give a high molar mass. However, it has hitherto not been possible to obtain isotactic polypropylene with complexes of this type, since the metal center did not have C2 symmetry. The resulting polypropylene was atactic with partially syndiotactic portions (WO 94/00500, U.S. Pat. No. 5,096,867, EP-A 520 732, U.S. Pat. No. 5 504 169).

Beside metallocenes having a cyclopentadienyl ring and a heteroatom as ligands, there are also known more complex systems, for example having a fluorenyl system and a heteroatom (Okuda et al., Organometallics 1995, 14, 789–795). However, the chiral metal atom is likewise not obtained. While U.S. Pat. No. 5,026,798 describes the synthesis of partially isotactic polypropylene using catalysts of this type, more recent investigations (A. L. McKnight et al. Organometallics 1997, 16, 2879–2885) show that identical systems achieve only isotacticities which are in the range of what was statistically expected. Thus, the ligand skeleton employed has no influence on the isotacticity.

It is an object of the present invention to remedy the disadvantages described above and to develop a metallocene complex which offers technical advantages in the polymerization of ethylene and shows, in particular, high incorporation of comonomers and affords a high molar mass. Furthermore, the metallocene should be capable of catalyzing the preparation of isotactic polypropylene, where it should likewise afford a high molar mass. Finally, the structure of the metallocene should be such that it can be prepared in a technically simple manner and that, in particular, a meso form which, for many applications, would have to be removed at great expense, can not be generated in the synthesis.

We have found that this object is achieved by the transition metal complexes defined at the outset. Furthermore, we have found processes for their preparation, compounds which are employed as intermediates for their preparation, the use of the transition metal complexes for polymerizing olefins, processes for polymerizing olefins, homo- or copolymers of ethylene or of propylene with other $C_2$–$C_{12}$-alk-1-enes, their use for preparing films, fibers or moldings, and the films, fibers or moldings made from these polymers.

The substituents $R^1$ to $R^3$ are preferably a hydrogen atom, a $C_1$–$C_6$-alkyl radical, such as methyl, ethyl, n-propyl, isopropyl, n-butyl, isobutyl, sec-butyl or tert-butyl, and also the various isomers of pentyl or hexyl, or an aryl radical, such as phenyl or naphthyl, which may be unsubstituted or substituted by alkyl radicals of the group just mentioned. Preference is likewise given to substituents $R^1$ to $R^3$, which form, with adjacent substituents $R^1$ to $R^3$ or with substituents of the bridge $A^1$, in each case with the linking atoms, a saturated or unsaturated ring having 5 to 10 carbon atoms.

Among the transition metals M in the formulae (Ia) and (Ib), preference is given to the elements of the 4th subgroup of the Periodic Table, i.e. titanium, zirconium and hafnium. Particular preference is given to titanium and zirconium.

Suitable ligands X are in particular the halogens, fluorine, chlorine, bromine and iodine, and particular preference is given to chlorine. Among the $C_1$–$C_{10}$-alkyl radicals, methyl, ethyl, propyl and butyl are particularly preferred. The preferred $C_6$–$C_{15}$-aryl radical is the phenyl radical.

The number n corresponds to the valency of M minus the number 2, i.e. for the complexes of titanium, zirconium or hafnium, n=2, for the complexes of vanadium, niobium or tantalum, n=3, and for the elements of the 3rd subgroup of the Periodic Table, i.e. scandium, yttrium and lanthanum, and of the lanthanoids, n=1.

Among the heteroligands Y, preference is given to —O—, —S— and

and substituents at the nitrogen atom which may be particularly mentioned are methyl, ethyl, n-propyl, isopropyl, n-butyl, tert-butyl, cyclohexyl, phenyl, benzyl and Si($R^8$)$_3$. Preferred substituents at the nitrogen atom also include radicals $R^7$ which are mono- or polysubstituted by groups acting as Lewis bases, such as si($R^8$)$_3$, $SR^8$, $OR^8$,

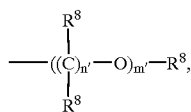

OSi($R^8$)$_3$, N($R^8$)$_2$, P($R^8$)$_2$ or combinations of these groups, where n' and m' are in each case the numbers 1, 2, 3 or 4. Particularly preferred groups here are $OR^8$ and N($R^8$)$_2$. Particularly preferred substituted radicals $R^7$ are substituted $C_1$–$C_{10}$-alkyl groups, in particular substituted methyl groups, ethyl groups, n-propyl groups, isopropyl groups, n-butyl groups, tert-butyl groups and cyclohexyl groups.

The bridge Z is usually a three-way organic or organometallic atom group which is attached, both directly and via the bridges A and $A^1$, to the cyclopentadienyl ring system and to the heteroligand Y.

Suitable bridges Z are, for example,

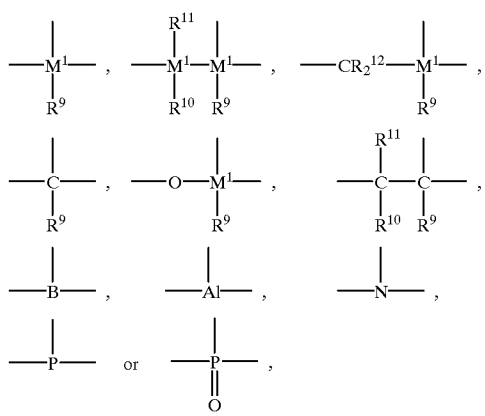

where
$R^9$ to $R^{12}$ are each hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or two radicals $R^9$ to $R^{12}$ together with the linking atoms, form a saturated or unsaturated ring having 4 to 15 carbon atoms, and
$M^1$ is silicon, germanium or tin.

Suitable bridges Z are, in particular, the radicals

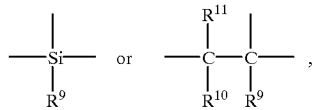

in which
$R^9$ to $R^{11}$ are methyl, ethyl, tert-butyl or phenyl. The bridge z is particularly preferably Si(Me), Si(Ph), Si(t-Bu) or C($CH_3$)$_2$C($CH_3$).

The two-way bridges A and $A^1$ effect a second link of the bridge Z to the cyclopentadienyl ring system. Thus, the "right" and the "left" side of the metallocene complex differ, and generation of a stereoselective polymerization center is possible.

The bridge A may for its part consist of several two-way bridges $A^2$, and A is preferably —($A^2$)$_m$— where m is from 1 to 6. Particularly preferably, the bridge A comprises from 1 to 3 $A^2$ members and in particular 2 $A^2$ members.

In general, the A¹ or A² members are organic or organometallic atom groups which preferably consist either of a substituted bridge atom or of a substituted or unsubstituted aromatic ring. A¹ and A² are, for example,

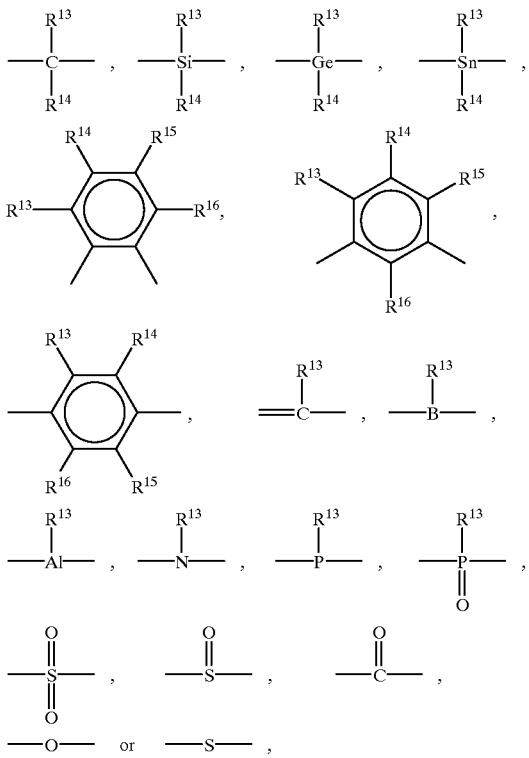

where A¹ and the individual members A² of A are identical or different, and $R^{13}$ to $R^{16}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or where two adjacent radicals in each case with the linking atoms form a saturated or unsaturated ring having 5 to 15 carbon atoms, or where a radical $R^{13}$ to $R^{16}$ of A¹ together with an adjacent radical $R^2$ or $R^3$ form a saturated or unsaturated ring system which has 5 to 15 carbon atoms, including the linking atoms.

The members A¹ or A² preferably contain the bridge atoms carbon, silicon, nitrogen or oxygen. Preferred substituents at the bridge atoms are hydrogen, methyl, ethyl and phenyl. Preference is also given to phenyl rings which may carry, as preferred substituents, methyl, ethyl or phenyl groups.

Particular preference is given to transition metal complexes of the formula (Ia) or (Ib) in which the group A¹ together with an adjacent radical $R^2$ or $R^3$ forms a saturated or unsaturated ring. Very particular preference is given here to transition metal complexes of the formula (Ia'),

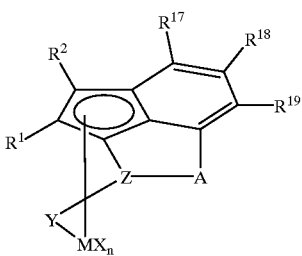

(Ia')

in which the groups A¹ and $R^3$ of the formula (Ia) together form an unsaturated ring having 6 carbon atoms and $R^{17}$ to $R^{19}$ are each a hydrogen atom, a $C_1$–$C_{10}$-alkyl group, a 5- to 7-membered cycloalkyl group, which may in turn be substituted by $C_1$–$C_{10}$-alkyl, are a $C_6$–$C_{15}$-aryl group or an arylalkyl group, or where two adjacent radicals in each case with the linking atoms form a saturated or unsaturated ring having 5 to 15 carbon atoms, or are $Si(R^4)_3$.

The substituents $R^{17}$ to $R^{19}$ are preferably a hydrogen atom, a $C_1$–$C_6$-alkyl radical, such as methyl, ethyl, n-propyl, isopropyl, n-butyl, isobutyl, sec-butyl or tert-butyl, and the various isomers of pentyl or hexyl, or an aryl radical, such as phenyl or naphthyl, which may be unsubstituted or substituted by alkyl radicals from the group just mentioned. Preference is also given to adjacent substituents $R^{17}$ to $R^{19}$ which, in each case with the linking atoms, form a saturated or unsaturated ring having 5 to 10 carbon atoms.

The transition metal complexes according to the invention can be present as such. However, it is also possible that, in addition to the ligands X, Y and the cyclopentadienyl ring system, 1 to 3 neutral Lewis bases, such as tetrahydrofuran, diethyl ether, trimethylamine or N,N-dimethylaniline, are coordinated to the transition metal atom. It is also possible that the transition metal complexes are present as dimers.

For preparing the transition metal complexes according to the invention, a process has been found which comprises reacting cyclopentadiene compounds of the formula (IIa) or (IIb),

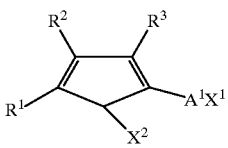

(IIa)

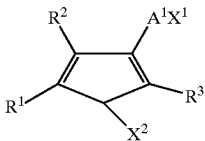

(IIb)

in which
$R^1$ to $R^3$ and $A^1$ are each as defined above and
$X^1$ is hydrogen or a halogen and
$X^2$ is hydrogen or a radical of the formula $M^2R^{20}_{(o-1)}$ in which
$M^2$ is an element of the 1st–4th main group of the Periodic Table,
$R^{20}$ is a halogen, a $C_1$–$C_{10}$-alkyl group, a 5- to 7-membered cycloalkyl group, which may in turn be substituted by $C_1$–$C_{10}$-alkyl, is a $C_6$–$C_{15}$-aryl group or an arylalkyl group, where the radicals $R^{20}$ may be identical or different, and o is the valency of $M^2$, with compounds of the formula (III)

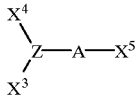
(III)

in which
Z and A are each as defined above,
$X^3$ and $X^4$ are each a halogen and
$X^5$ is hydrogen, a halogen or a group

where
$R^{21}$ and $R^{22}$ are each hydrogen, $C_1$–$C_{10}$-alkyl, $C_3$–$C_{10}$-cycloalkyl or $C_6$–$C_{15}$-aryl, to give compounds of the formula (IVa) or (Ivb),

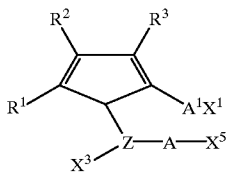
(IVa)

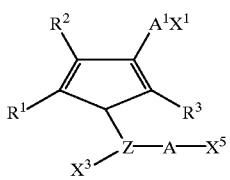
(IVb)

preparing from these by intramolecular ring closure the compounds of the formula (Va) or (Vb),

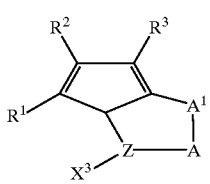
(Va)

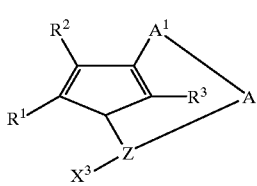
(Vb)

which are converted into compounds of the formula (VIa) or (VIb),

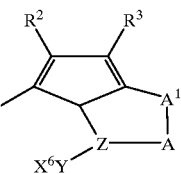
(VIa)

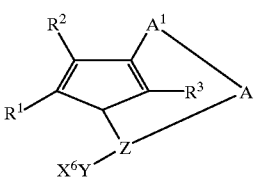
(VIb)

in which
$X^6$ is hydrogen or a radical of the formula $M^3R^{23}_{(p-1)}$, in which, $M^3$ is an element of the 1st–4th main group of the Periodic Table, $R^{23}$ is a halogen, a $C_1$–$C_{10}$-alkyl group, a 5- to 7-membered cycloalkyl group, which may in turn be substituted by $C_1$–$C_{10}$-alkyl, is a $C_6$–$C_{15}$-aryl group or an arylalkyl group, where the radicals $R^{23}$ may be identical or different, and p is the valency of $M^3$, which are then converted into the transition metal complexes of the formula (Ia) or (Ib).

A preferred process for preparing the transition metal complexes according to the invention comprises reacting indene compounds of the formula (IIa')

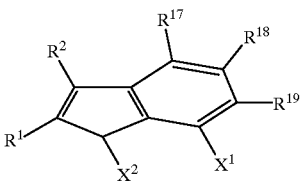
(IIa')

in which $X^1$, $X^2$, $R^1$, $R^2$ and $R^{17}$ to $R^{19}$ are each as defined above, with a compound of the formula (III) to give compounds of the formula (IVa'),

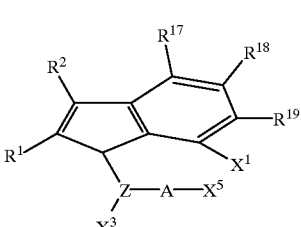
(IVa')

in which $X^3$, $X^5$, Z and A are each as defined above, from which, by intramolecular ring closure, the compounds of the general formula (Va') are prepared, (Va')

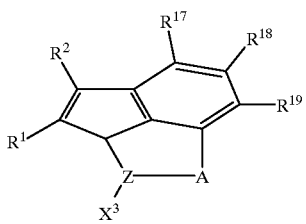

which are reacted to give compounds of the formula (VIa')

(VIa')

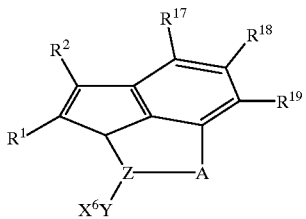

in which $X^6$ and Y are each as defined above,
which are then converted into the transition metal complexes of the formula (Ia').

The starting materials (IIa), (IIa') and (IIb) and also (III) are known or can be prepared in a known manner. Some of them are commercially available.

They can be reacted by the customary methods of substitution on cyclopentadiene systems, generally in solvents, where preference is given to using ethereal solvents, such as diethyl ether or THF. The addition sequence per se is immaterial. Preference is given to initially charging the compounds (IIa), (IIa') or (IIb) in the solvent and to adding the compound or the compounds (III) neat or in solution. This can be carried out at from −100 to +100° C., preferably from −80 to +30° C. The products (Iva), (Iva') or (IVb) can then be obtained, for example, by extraction (in the case of one or more other solid reaction products) or by distillation (in the case of one or more other liquid reaction products).

The intramolecular ring closure to the compounds (Va), (Va') or (Vb) can generally be carried out by the known methods of C—C, C-heteroatom or heteroatom-heteroatom bond formation, as described, for example, in Jerry March, Advanced Organic Chemistry, John Wiley & Sons, New York 1985 or Organikum, VEB Deutscher Verlag der Wissenschaften, Berlin 1977. Depending on the nature of the radicals $A^1$, $X^1$, A and $X^5$, particularly suitable reactions which may be mentioned are Friedel-Crafts alkylation, Friedel-Crafts acylation, azo coupling, radical bond formation, Wurz reaction, addition of a heteroatom-hydrogen bond to a C—C, C-heteroatom or heteroatom-heteroatom multiple bond (for example hydrosilylation, hydroboration, hydroamination), formation of Schiff bases, formation of amides, esterification (also organometal-catalyzed), etherification, Grignard reaction, McMurry coupling, Diels-Alder reaction, cross-coupling of aromatics, Heck reaction, Suzuki coupling, Reformatsky reaction, Wittig reaction, Ritter reaction and condensation reactions (for example aldol condensation, Knoevenagel condensation, Perkin reaction). In the case of compounds of the formula (IVa'), particular preference is given to the reactions Friedel-crafts alkylation or Friedel-Crafts acylation. The Friedel-Crafts alkylation can also be carried out as a two-step synthesis, starting from the unsaturated compound and the in situ formation of the appropriately halogenated precursor.

The compounds (Va), (Va') or (Vb) are subsequently reacted with compounds of the formula $YX^6X^7$ in which
Y is —O—, —S—,

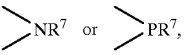

where,
$R^7$ is $C_1$–$C_{10}$-alkyl, $C_6$–$C_{15}$-aryl, $C_3$–$C_{10}$-cycloalkyl or $C_7$–$C_{18}$-alkylaryl or is $C_1$–$C_{10}$-alkyl, $C_6$–$C_{15}$-aryl, $C_3$–$C_{10}$-cycloalkyl or $C_7$–$C_{18}$-alkylaryl, each of which is mono- or polysubstituted by $Si(R^8)_3$, $SR^8$, $OR^8$,

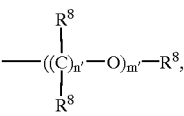

$OSi(R^8)_3$, $N(R^8)_2$, $P(R^8)_2$ or a combination thereof, or is $Si(R^8)_3$ where
n' and m' are each 1, 2, 3 or 4 and
$R^8$ is hydrogen, $C_1$–$C_{10}$-alkyl, $C_6$–$C_{15}$-aryl, which may in turn be substituted by $C_1$–$C_4$-alkyl groups, or is $C_3$–$C_{10}$-cycloalkyl,
where the radicals $R_8$ are identical or different, and
$X^6$ and $X^7$ is hydrogen or a radical of the formula $M^3R^{23}_{(p-1)}$, in which,
$M^3$ is an element of the 1st–4th main group of the Periodic Table,
$R^{23}$ is a halogen, a $C_1$–$C_{10}$-alkyl group, a 5- to 7-membered cycloalkyl group, which may in turn be substituted by $C_1$–$C_{10}$-alkyl, is a $C_6$–$C_{15}$-aryl group or an arylalkyl group, where the radicals $R^{23}$ may be identical or different, and
p is the valency of $M^3$.

By reacting $YX^6X^7$ with the radical $X^3$, an equivalent of a compound of the formula $X^7X^3$ is cleaved off with formation of the bond between Z and Y. Preferred compounds of the formula $YX^6X^7$ are monosubstituted amines and alcohols or their organometal derivatives, and particular preference is given to methylamine, ethylamine, tert-butylamine and phenylamine. If an acid is liberated during the reaction (i.e. $X^7$ is a hydrogen), a base is usually added to the reaction mixture.

The reaction is generally carried out in solution, and preference is given to using ethereal solvents, such as diethyl ether or THF. The addition sequence per se is immaterial. Preference is given to initially charging the compound (Va), (Va') or (Vb) in the solvent and to adding the compound $YX^6X^7$ neat, in solution or in the form of a hydrosalt (for example a hydrochloride) which is then converted into the corresponding base using a strong base. This can be carried out at from −100 to +100° C., preferably from −80 to +70° C. When amines are employed, it has been found to be advantageous to employ an excess of double the amount of amine, since it acts in this case simultaneously as base.

The resulting compounds (VIa), (VIa') or (VIb) can be converted by known methods into the corresponding metal complexes. The complexation methods are described, for example, in EP-A 416 815, EP-A 420 436 or Okuda et al., Organometallics 14, (1995), 789–795. Preference is given to using the compounds (VIa), (VIa') or (VIb) where $X^6$=Li. The reaction can be carried out, for example, using tetrasubstituted Ti—, Zr— or Hf compounds. Preferred metals are titanium and zirconium. Preferred substituents are halogens, in particular chlorine. The tetrahalides can also be employed in the form of base adducts (for example with THF).

The reaction is generally carried out in solution, and preference is given to using ethereal solvents, such as diethyl ether or THF. The addition sequence per se is immaterial. Preference is given to initially charging the compounds (VIa), (VIa') or (VIb) in the solvent and adding the metal compound neat or in solution. This can be carried out at temperatures of from −100 to +100° C., preferably from −80 to +30° C.

The transition metal complexes (Ia), (Ia') and (Ib) according to the invention have an asymmetric arrangement of the ligands at the metal atom. Owing to this structure, the transition metal complexes (Ia), (Ia') and (Ib) can not be present in a meso form. However, as a result of the unsymmetric substitution at the cyclopentadienyl ligand, the polymerization proceeds stereoselectively.

The present invention furthermore relates to the intermediates, employed for preparing the transition metal complexes (Ia') according to the invention, of the formula (VIa')

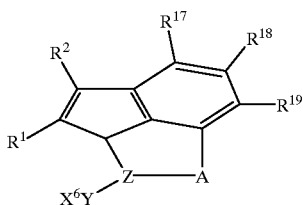

(VIa')

in which the substituents and indices have the following meanings:

$R^1$, $R^2$ and $R^{17}$ to $R^{19}$ are hydrogen, $C_1$–$C_{10}$-alkyl, 5- to 7-membered cycloalkyl, which in turn may be substituted by $C_1$–$C_{10}$-alkyl, are $C_6$–$C_{15}$-aryl or arylalkyl, where two adjacent radicals, in each case with the linking atoms, may form a saturated or unsaturated ring having 5 to 15 carbon atoms, or are si($R^4$)$_3$ where $R^4$ is $C_1$–$C_{10}$-alkyl, $C_3$–$C_{10}$-cycloalkyl or $C_6$–$C_{15}$-aryl, $X^6$ is hydrogen or a radical of the formula $M^3R^{23}_{(p\text{-}l)}$, in which $M^3$ is an element of the 1st–4th main group of the Periodic Table, $R^{23}$ is a halogen, a $C_1$–$C_{10}$-alkyl group, a 5- to 7-membered cycloalkyl group, which in turn may be substituted by $C_1$–$C_{10}$-alkyl, is a $C_6$–$C_{15}$-aryl group or an arylalkyl group, where the radicals $R^{23}$ may be identical or different, and P is the valency of $M^3$, Y is —O—, —S—,

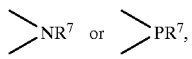

where $R^7$ is $C_1$–$C_{10}$-alkyl, $C_6$–$C_{15}$-aryl, $C_3$–$C_{10}$-cycloalkyl or $C_7$–$C_{18}$-alkylaryl or is $C_1$–$C_{10}$-alkyl, $C_6$–$C_{15}$-aryl, $C_3$–$C_{10}$-cycloalkyl or $C_7$–$C_{18}$-alkylaryl, each of which is mono- or polysubstituted by Si($R^8$)$_3$, $SR^8$, $OR^8$,

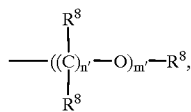

OSi($R^8$)$_3$, N($R^8$)$_2$, P($R^8$)$_2$ or a combination thereof, or is Si($R^8$)$_3$ where n' and m' are each 1, 2, 3 or 4 and $R^8$ is hydrogen, $C_1$–$C_{10}$-alkyl, $C_6$–$C_{15}$-aryl, which may in turn be substituted by $C_1$–$C_4$-alkyl groups, or is $C_3$–$C_{10}$-cycloalkyl, where the radicals $R^8$ are identical or different,

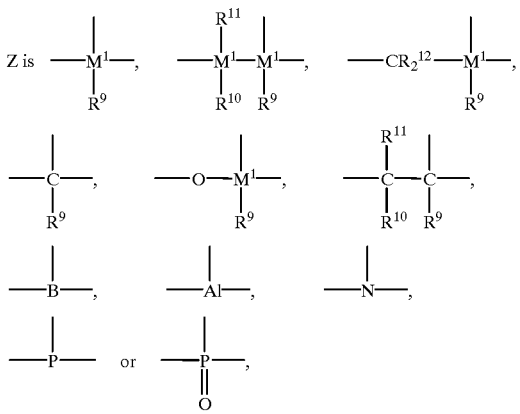

where $R^9$ to $R^{12}$ are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or where two adjacent radicals, in each case with the linking atoms, form a saturated or unsaturated ring having 4 to 15 carbon atoms, and, $M^1$ is silicon, germanium or tin, and A is a bridge —$(A^2)_m$— where m is from 1 to 6, and

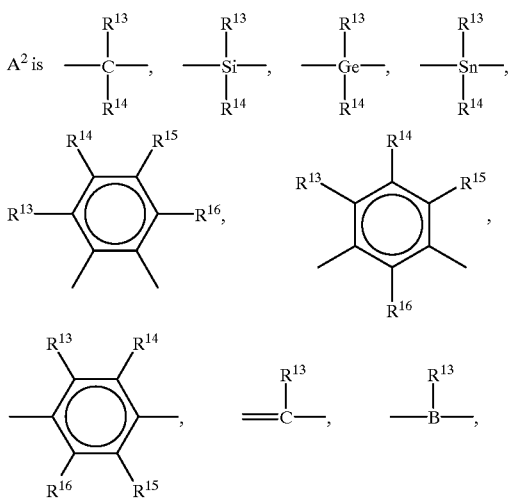

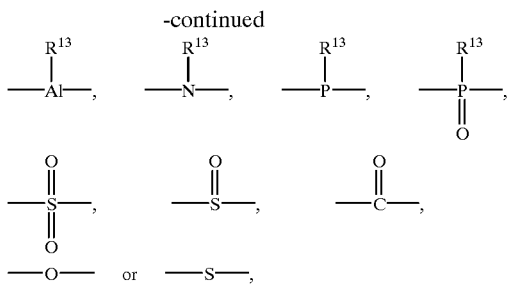

where the individual members $A^2$ of A are identical or different.

The present invention furthermore also relates to the intermediates, employed for preparing the transition metal complexes Ia' according to the invention, of the formula (IVa')

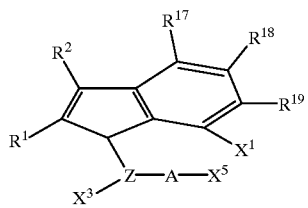

(IVa')

in which the substituents and indices have the following meanings:

$R^1$, $R^2$ and $R^{17}$ to $R^{19}$ are hydrogen, $C_1$–$C_{10}$-alkyl, 5- to 7-membered cycloalkyl, which in turn may be substituted by $C_1$–$C_{10}$-alkyl, $C_6$–$C_{15}$-aryl or arylalkyl, where two adjacent radicals, in each case with the linking atoms, may form a saturated or unsaturated ring having 5 to 15 carbon atoms, or are $Si(R^4)_3$ where $R^4$ is $C_1$–$C_{10}$-alkyl, $C_3$–$C_{10}$-cycloalkyl or $C_6$–$C_{15}$-aryl, $X^1$ is hydrogen or a halogen, $X^3$ is a halogen and $X^5$ is hydrogen, a halogen or a group

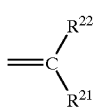

where $R^{21}$ and $R^{22}$ are each hydrogen, $C_1$–$C_{10}$-alkyl, $C_3$–$C_{10}$-cycloalkyl or $C_6$–$C_{15}$-aryl,

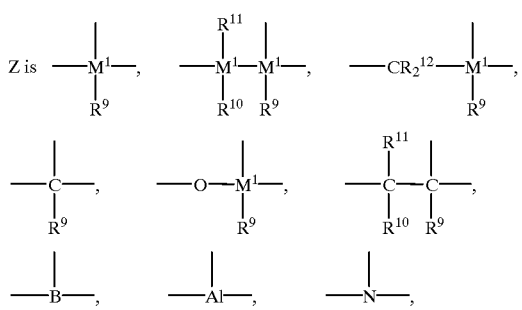

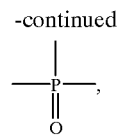

where $R^9$ to $R^{12}$ are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or where two adjacent radicals, in each case with the linking atoms, form a saturated or unsaturated ring having 4 to 15 carbon atoms, and $M^1$ is silicon, germanium or tin, and A is a bridge —$(A^2)_m$— where m is from 1 to 6, and

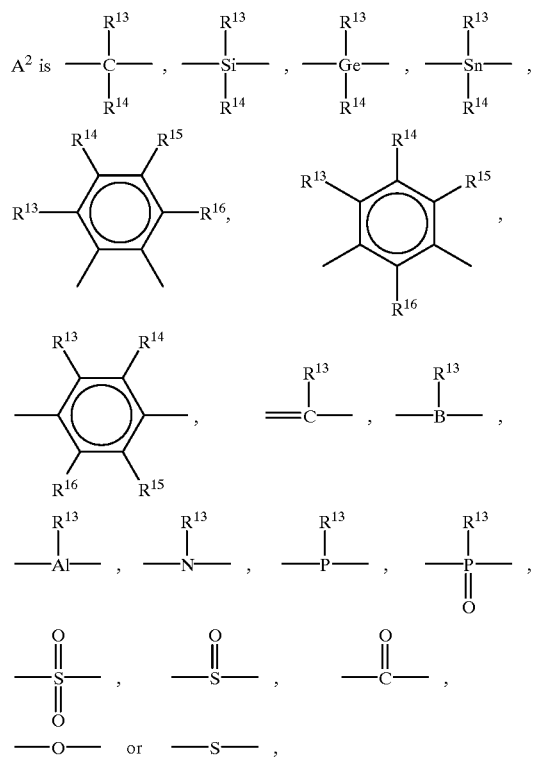

where the individual members $A^2$ of A are identical or different.

The transition metal complexes according to the invention are suitable, for example, for polymerizing olefins and in particular for polymerizing α-olefins, i.e. hydrocarbons having terminal double bonds. Suitable monomers can be functionalized olefinically unsaturated compounds, such as ester or amide derivatives of acrylic or methacrylic acid, for example acrylates, methacrylates or acrylonitrile. Preference is given to non-polar olefinic compounds, including aryl-substituted α-olefins such as styrene. Particularly preferred α-olefins are linear or branched $C_2$–$C_{12}$-alk-1-enes, in particular linear $C_2$–$C_{10}$-alk-1-enes, such as ethylene, propylene, but-1-ene, pent-1-ene, hex-1-ene, hept-1-ene, oct-1-ene, non-1-ene, dec-1-ene or 4-methylpent-1-ene. It is also possible to polymerize mixtures of these monomers.

The present invention furthermore relates to a process for polymerizing olefins, which comprises carrying out the polymerization in the presence of transition metal complexes of the formulae (Ia), (Ia') or (Ib) and metallocenium-ion-forming compounds.

Suitable metallocenium-ion-forming compounds are, for example, strong neutral Lewis acids, ionic compounds having Lewis-acidic cations or ionic compounds having Brönsted acids as cations.

Preferred strong neutral Lewis acids are compounds of the formula (VII)

$$M^4X^8X^9X^{10} \qquad (VII)$$

in which
- $M^4$ is an element of the IIIrd main group of the Periodic Table, in particular B, Al or Ga, preferably B,
- $X^8$, $X^9$ and $X^{10}$ are hydrogen, $C_1$–$C_{10}$-alkyl, $C6$–$C_{15}$-aryl, alkylaryl, arylalkyl, haloalkyl or haloaryl having in each case 1 to 10 carbon atoms in the alkyl radical and 6 to 20 carbon atoms in the aryl radical, or fluorine, chlorine, bromine or iodine, and are in particular haloaryls, preferably pentafluorophenyl.

Particular preference is given to compounds of the formula (VII), in which $X^8$, $X^9$ and $X^{10}$ are identical, preferably tris(pentafluorophenyl)borane.

Suitable ionic compounds having Lewis-acidic cations are compounds of the formula (VIII)

$$[(Y_1^{a+})Q_1Q_2 \ldots Q_z]^{d+} \qquad (VIII)$$

in which
- $Y_1$ is an element of the Ist to the VIth main group or the Ist to the VIIIth subgroup of the Periodic Table,
- $Q_1$ to $Q_z$ are radicals carrying one negative charge, such as $C_1$–$C_{28}$-alkyl, $C_6$–$C_{15}$-aryl, alkylaryl, arylalkyl, haloalkyl, haloaryl, having in each case 6 to 20 carbon atoms in the aryl and 1 to 28 carbon atoms in the alkyl radical, $C_3$–$C_{10}$-cycloalkyl, which may be $C_1$–$C_{10}$-alkyl-substituted, halogen, $C_1$–$C_{28}$-alkoxy, $C_6$–$C_{15}$-aryloxy, silyl or mercaptyl groups,
- a is an integer from 1 to 6 and
- z is an integer from 0 to 5,
- d is the difference a–z, and is greater than or equal to 1.

Particularly suitable cations are carbonium cations, oxonium cations and sulfonium cations, and also cationic transition metal complexes. The triphenylmethyl cation, the silver cation and the 1,1'-dimethylferrocenyl cation should be mentioned in particular. They preferably have non-coordinating counterions, in particular boron compounds as also mentioned in WO 91/09882, preferably tetrakis(pentafluorophenyl)borate.

Ionic compounds with Brönsted acids as cations and preferably likewise non-coordinating counterions are mentioned in Wo 91/09882, and a preferred cation is N,N-dimethylanilinium.

The amount of strong, neutral Lewis acids, of ionic compounds having Lewis-acidic cations or of ionic compounds having Brönsted acids used in the process according to the invention as cations is preferably from 0.1 to 10 equivalents, based on the transition metal complex (Ia), (Ia') or (Ib).

Particularly suitable metallocenium-ion-forming compounds are open-chain or cyclic aluminoxane compounds of the formulae (IX) or (X)

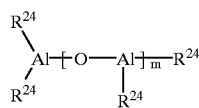

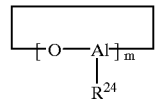

where $R^{24}$ is a $C_1$–$C_4$-alkyl group, preferably a methyl or ethyl group, and m is an integer from 5 to 30, preferably from 10 to 25.

These oligomeric aluminoxane compounds are generally prepared by reacting a solution of trialkylaluminum with water, as described, inter alia, in EP-A 284 708 and U.S. Pat. No. 4,794,096.

The oligomeric aluminoxane compounds thus obtained are generally mixtures of both linear and cyclic molecules of different chain length, and m is therefore to be regarded as an average value. The aluminoxane compounds may also be present in a mixture with other metal alkyl compounds, preferably with alkylaluminum compounds.

It has proven advantageous to use amounts of the transition metal complexes (Ia), (Ia') or (Ib) and of the oligomeric aluminoxane compounds of the formulae (IX) or (X) which give an atomic ratio of aluminum from the oligomeric aluminoxane compounds to transition metal from the transition metal complexes in the range from 10:1 to $10^6$:1, in particular from 10:1 to $10^4$:1.

It is moreover possible to use, instead of the aluminoxane compounds of the formulae (IX) or (X), aryloxyalumoxanes, as described in U.S. Pat. No. 5,391,793, aminoaluminoxanes, as described in U.S. Pat. No. 5,371,260, aminoaluminoxane hydrochlorides, as described in EP-A 633 264, siloxyaluminoxanes, as described in EP-A 621 279, or mixtures of these, as metallocenium-ion-forming compounds.

In the process according to the invention, preference is given to using both the transition metal complexes (Ia), (Ia') or (Ib) and the metallocenium-ion-forming compounds in solution, particular preference being given to aromatic hydrocarbons having 6 to 20 carbon atoms, in particular xylenes and toluene.

Suitable for use as a further component are additionally also metal compounds of the formula (XI)

$$M^5(R^{25})_r(R^{26})_s(R^{27})_t \qquad (XI)$$

in which
- $M^5$ is an alkali metal, an alkaline earth metal or a metal of the IIIrd main group of the Periodic Table, i.e. boron, aluminum, gallium, indium or thallium,
- $R^{25}$ is hydrogen, $C_1$–$C_{10}$-alkyl, $C_6$–$C_{15}$-aryl, alkylaryl or arylalkyl having in each case 1 to 10 carbon atoms in the alkyl radical and 6 to 20 carbon atoms in the aryl radical,
- $R^{26}$ and $R^{27}$ are hydrogen, halogen, $C_1$–$C_{10}$-alkyl, $C6$–$C_{15}$-aryl, alkylaryl, arylalkyl or alkoxy having in each case 1 to 10 carbon atoms in the alkyl radical and 6 to 20 carbon atoms in the aryl radical,
- r is an integer from 1 to 3 and
- s and t are integers from 0 to 2, and the total r+s+t corresponds to the valence of $M^5$.

Among the metal compounds of the formula (XI), preference is given to those in which $M^5$ is lithium, magnesium or aluminum, and $R^{26}$ and $R^{27}$ are $C_1$–$C_{10}$-alkyl.

Particularly preferred metal compounds of the formula (XI) are n-butyllithium, n-butyl-n-octylmagnesium, n-butyl-n-heptyl magnesium, tri-n-hexylaluminum, triisobutylaluminum, triethylaluminum and trimethylaluminum.

If a metal compound of the formula (XI) is employed, it is preferably present in the catalyst system in an amount which gives the molar ratio of $M^5$ from formula (XI) to transition metal M from formula (Ia), (Ia') or (Ib) of from 800:1 to 1:1, in particular from 500:1 to 50:1.

In the polymerization process according to the invention, the transition metal complexes (Ia), (Ia') or (Ib) can also be used on a support material.

The support materials used are preferably finely divided supports which generally have a particle diameter in the range from 1 to 300 μm, in particular from 20 to 90 μm. Examples of suitable support materials are inorganic oxides of silicon, of aluminum, of titanium, or of one of the metals of the Ist or IInd main group of the Periodic Table, or mixtures of these oxides, among which, besides alumina and magnesium oxide and phyllosilicates, preference is in particular given to silica gel.

The carrier may be subjected to a thermal treatment, for example in order to remove adsorbed water, such a treatment generally being carried out at temperatures in the range of from 80 to 200° C., preferably of from 100 to 150° C., or the support may be calcined. The support may also be treated chemically, in which case customary drying agents, such as metal alkyl compounds, preferably aluminum alkyl compounds, chlorosilanes or $SiCl_4$, are generally employed.

Other suitable supports are finely divided polyolefins, for example finely divided polypropylene.

The process according to the invention may be carried out in the reactors which are usual for polymerizing olefins, either batchwise or preferably continuously. Examples of suitable reactors are continuously-operated stirred tank reactors, agitated powder bed reactors, loop reactors or fluidized-bed reactors, and it is possible, if desired, to use a series of two or more identical or different reactors connected in series. The polymerization reactions may be carried out in the gas phase, in suspension, in liquid and in supercritical monomers, or in inert solvents.

The polymerization conditions are not critical per se. Pressures of from 1 to 3500 bar, preferably from 2 to 100 bar and in particular from 10 to 40 bar have proven suitable, as have temperatures of from 0 to 400° C., preferably from 20 to 250° C. and in particular from 50 to 100° C.

The average molar mass of the polymers may be controlled using the methods which are customary in polymerization technology, for example by introducing regulators such as hydrogen.

Particularly preferably, the transition metal complexes according to the invention can be employed for preparing homo- or copolymers of ethylene or of propylene with other $C_2$–$C_{12}$-alk-1-enes.

The homo- or copolymers of propylene with other $C_2$–$C_{12}$-alk-1-enes which homo- or copolymers are obtainable using the transition metal complexes (Ia), (Ia') or (Ib) are particularly preferably homopolymers of propylene or copolymers of propylene with ethylene and/or but-1-ene. The copolymers of propylene may have a random structure. However, they may also be present in the form of block copolymers or impact copolymers. The homo- or copolymers of propylene are distinguished by a high molar mass and in particular by an isotactic structure of the polymer chains.

The homo- or copolymers of ethylene with other $C_2$–$C_{12}$-alk-1-enes which homo- or copolymers are obtainable using the transition metal complexes (Ia), (Ia') or (Ib) are particularly preferably homopolymers of ethylene or copolymers of ethylene with propylene, but-1-ene, hex-1-ene and/or oct-1-ene. The homo- or copolymers of ethylene are distinguished by a very high molar mass. During their preparation, a high rate of comonomer incorporation is observed, owing to which copolymers having a high comonomer content are obtainable, or it is possible to obtain the desired copolymers using a monomer mixture which has a relatively low comonomer content and therefore offers technical advantages in the polymerization.

The homo- or copolymers of ethylene or of propylene with other $C_2$–$C_{12}$-alk-1-enes which homo- or copolymers are obtainable using the transition metal complexes according to the invention have good technical properties and are suitable for preparing fibers, films or moldings.

EXAMPLES

Example 1

Synthesis of Ligands and Metallocene Complex

All syntheses were carried out with exclusion of air and moisture. The reagents, the solvents and the equipment were prepared accordingly. The reaction scheme is depicted in FIG. 1.

a) Synthesis of Fluorenyllithium (Compound II)

With stirring, 113 ml of a 1.6 M solution of n-butyllithium in hexane (0.18 mol) were added to a solution of 25 g (0.15 mol) of fluorene in 220 ml of diethyl ether. To bring the reaction to completion, the mixture was boiled under reflux for 6 h and then stirred at room temperature overnight. The solvent was subsequently removed under reduced pressure and the resulting yellow powder was washed repeatedly with petroleum ether and dried under reduced pressure. This gave fluorenyllithium (compound II) in almost quantitative yield.

b) Synthesis of Allylchlorofluorenylmethylsilane (Compound IV)

8.6 g (50 mmol) of compound II were dissolved in 250 ml of diethyl ether. At room temperature and with stirring, 11.1 g (72 mmol) of allyldichlorosilane (compound III) were added to this mixture, which was then stirred at room temperature for a further 3 h. The solvent was subsequently completely removed under reduced pressure and the residue was taken up in 200 ml of petroleum ether. The lithium chloride was centrifuged off, the supernatant was concentrated to a volume of about 20 ml and the reaction product was crystallized at −78° C. The yield was 8.59 g (60.4%).

$^1$H NMR (CDCl$_3$) δ (ppm): 0.29 (s, 3H, Pos.1), 1.56 (AB System, 2H, Pos.2), 4.16 (s, 1H, Pos.5), 4.83 (dm, 1H. Pos.4), 4.86 (dm, 1H, Pos.4), 5.49 (m, 1H, Pos.3), 7.35 (m, 2H, Pos.B,B',C,C'), 7.41 (t, 2H, Pos.B,B',C,C'), 7.69 (m, 2H, Pos.A,A',D,D'), 7.87 (d, 2H, Pos.A,A',D,D')

Figure 2:
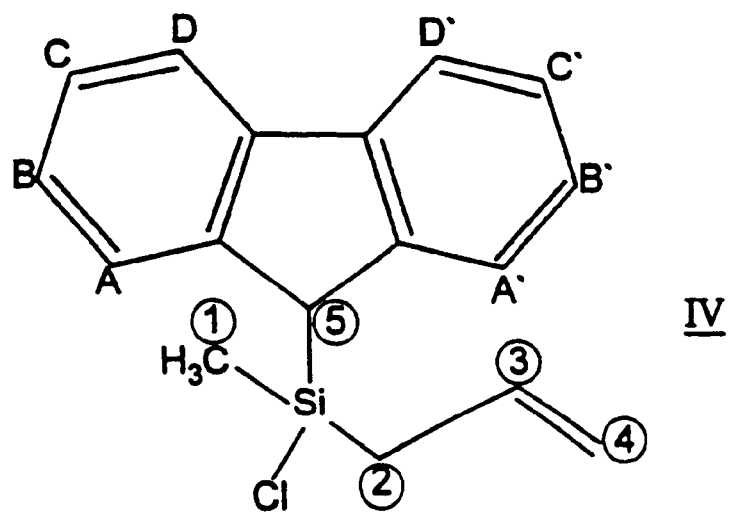

The assignment of the NMR signals is shown in FIG. 2.

c) Synthesis of 10-chloro-10,12-dimethyl-9,1-silapropanofluorene (Compound V)

8.59 g (30 mmol) of compound IV were dissolved in 150 ml of benzene. With stirring, this solution was added to a suspension of 4.5 g (34 mmol) of aluminum chloride and 150 ml of benzene which had been admixed with a drop of 37% strength HCl. The mixture was stirred at room temperature for 3 h, then 6 ml (4.68 g, 40 mmol) of tetraethylmethylenediamine (THEDA) were added, and then the aluminum chloride-THEDA complex that formed precipitated out. The supernatant was decanted off, the solvent was removed under reduced pressure and the residue was taken up in 200 ml of petroleum ether. The undissolved components were separated off by centrifugation and the supernatant was concentrated to about 30 ml and crystallized at −78° C. The resulting substance was recrystallized from petroleum ether. This gave a white solid. The yield was 2.31 g (27%).

$^1$H NMR (CDCl$_3$) δ (ppm): −0.45 (s, 3H, Pos.5), 0.52–0.59 (m, 2H, Pos.4), 1.35 (s, 3H, Pos.3), 2.95 (sept, 1H, Pos.2), 3.75 (s, 1H, Pos.1), 7.05–7.85 (m, 7H, arom.H)

$^{13}$C NMR (CDCl$_3$) δ (ppm): −2.41 (q, J=123.2 Hz, Pos.A), 20.4 (q, J=125.9Hz, Pos.B), 25.5 (t, Pos.C), 31.7 (d, J=122.7 Hz, Pos.D), 40.6 (d, J=129 Hz, Pos.E), 118.4, 120.8, 121.9, 124.4, 126.6, 127.2, 128.0 (d, J=160 Hz, Pos.F), 140.4, 140.5, 141.5, 142.1, 143.9 (s, quaternary carbon atoms)

Figure 3:
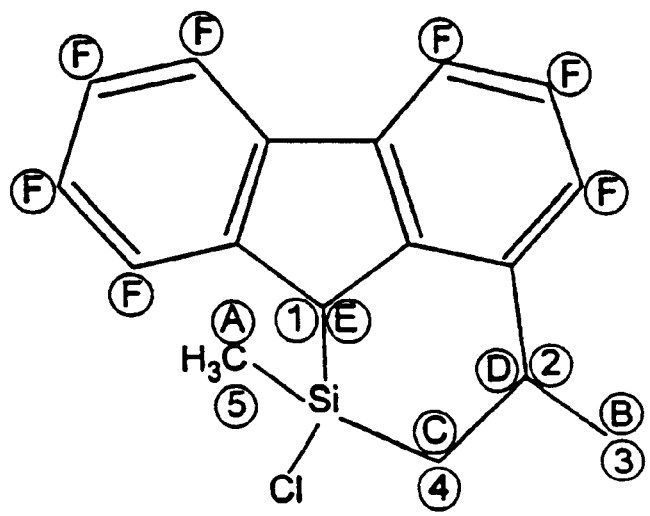

The assignment of the NMR signals is shown in FIG. 3.

Mass spectrometry (EI, 1 mA, 70 eV) (m/z, rel. int.): [M+] (284, 43); [M−C$_3$H$_6$$^+$] (242, 100)

CH analysis: C: calc.: 71.68, found.: 71.75; H: calc.: 6.01, found.: 5.94 d) Synthesis of 10-methyl-10-methylamino-12-methyl-9,1-sila-propanofluorene (Compound VI)

At room temperature and with stirring, methylamine, which was generated from methylammoniumhydrochloride and potassium hydroxide and dried using KOH pellets and calcium oxide was passed for 2 h through a solution of 2.31 g (8 mmol) of the compound V in 400 ml of diethyl ether. The mixture was stirred for a further 2 h and the solvent was then removed under reduced pressure. The residue was taken up in 200 ml of petroleum ether. The undissolved components were removed by centrifugation and the supernatant was concentrated and crystallized at −78° C. The yield was 1.1 g (49%).

e) Synthesis of the Metallocene Complex (Compound I)

1.03 g (3.7 mmol) of the compound VI were dissolved in 30 ml of diethyl ether and cooled to −78° C. Over a period of 20 min, 4.62 ml (7.4 mmol) of butyllithium (1.6 M in heptane) were added, and the mixture was stirred at −78° C. for 2 h and subsequently at room temperature for 2 h. The solvent of the orange solution was subsequently removed under reduced pressure and the residue was taken up in 30 ml of THF. At −78° C., a total of 1.79 g (4.75 mmol) of solid zirconium tetrachloride*2THF were added over a period of 40 min. With stirring, the mixture was allowed to slowly warm to room temperature. The solvent was subsequently removed under reduced pressure. After the addition of toluene, lithium chloride and excess zirconium tetrachloride*2THF were removed. Petroleum ether was added to the solution and the product was crystallized at −78° C. This gave an orange solid. The yield was 1.2 g (74%).

Example 2

Supporting of the Metallocene Complex

In a 50 ml flask with magnetic stirrer, 20 ml of toluene were initially charged. 109 mg (0.14 mmol) of N,N-dimethylanilinium tetrakis(pentafluorophenyl)borate, 60 mg (0.14 mmol) of compound I and 2.6 g of silica gel (ES 70X, from Crosfield) deactivated with triisobutylaluminum were added. The resulting mixture was heated at 80° C. for 1 h. The solvent was subsequently removed under reduced pressure. This gave about 2.8 g of supported catalyst.

Example 3

Ethylene Homopolymerization

In a stirred 1 l steel autoclave, which had been carefully flushed with nitrogen and thermostatted to the polymerization temperature of 70° C., 400 ml of isobutane and 170 mg of triethylaluminum were initially charged. 270 mg of the supported catalyst prepared in Example 2 and a further 6 ml of isobutane were then introduced, and ethylene was applied to give a total pressure of 38 bar. The pressure in the autoclave was kept constant by metering in more ethylene. After 90 min, the polymerization was terminated by venting the autoclave. 30 g of polymer in the form of a grit having good flowability and a viscosity (nvalue in accordance with ISO 1628-3 at 135° C. in Dekalin) of 10.07 dl/g were obtained.

Example 4

Ethylene/hex-1-ene Copolymerization

In a stirred 1 l steel autoclave, which had been carefully flushed with nitrogen and thermostatted to the polymerization temperature of 70° C., 500 ml of isobutane, 120 mg of triethylaluminum and 40 ml of hex-1-ene were initially charged. 50 mg of the supported catalyst and a further 6 ml of isobutane were then introduced, and ethylene was applied to give a total pressure of 38 bar. The pressure in the autoclave was kept constant by metering in more ethylene. After 90 min, the polymerization was terminated by venting the autoclave. 200 g of polymer in the form of a grit having good flowability and a viscosity (η value in accordance with ISO 1628-3 at 135° C. in Dekalin) of 4.23 dl/g and a hex-1-ene content (determined by IR spectroscopy) of 2.1% by weight were obtained.

Example 5

Propylene Polymerization

In a stirred 1 l steel autoclave, which has been carefully flushed with nitrogen, 500 ml of liquid propylene were initially charged. 3 ml of a methylaluminoxane solution (1.53 mol/l in toluene) were added. A mixture of 5 mg of the metallocene complex prepared in Example 1 and a further 6.5 ml of the methylaluminoxane solution were subsequently added. The autoclave was then heated to 60° C. A pressure of 26 bar resulted. The pressure was kept constant by metering in additional propene.

After 90 min, the polymerization was terminated by venting the autoclave. This gave 1 g of polymer as a white powder. The melting temperature (determined by DSC) was 148° C., the proportion of mmmm-pentads (determined by $^{13}$C NMR spectroscopy) was 61% and the viscosity (η value, determined in accordance with ISO 1628-3 at 135° C. in Dekalin) was 3.01 dl/g.

Example 6

Synthesis of Ligands and Metallocene Complexes

Figure 4:
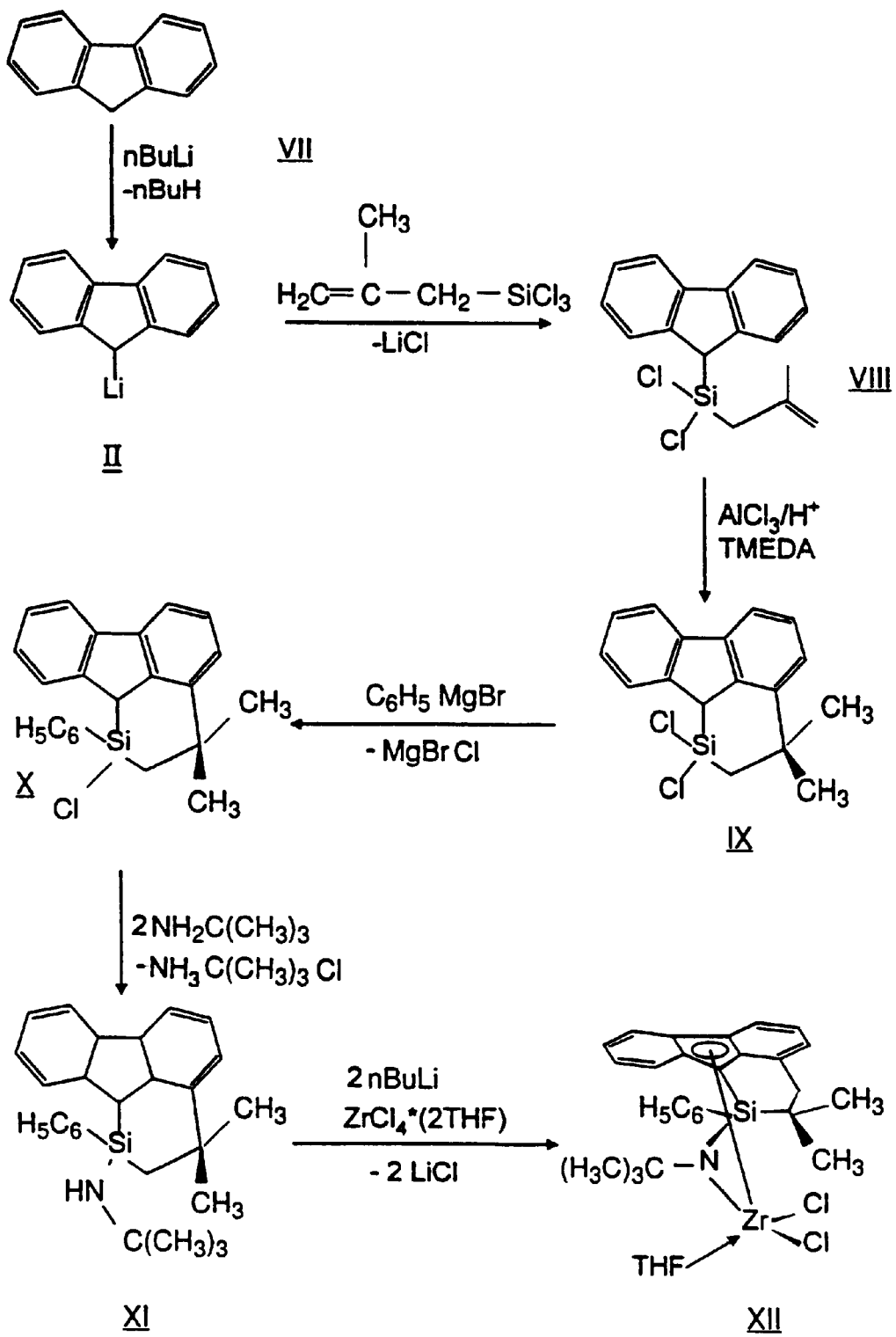

All syntheses were carried out under exclusion of air and moisture. The reagents, solvents and apparatuses were prepared correspondingly. The reaction scheme is shown in FIG. 4.

a) Synthesis of dichlorofluorenyl-β-methallylsilane (Compound VIII)

13.01 g (75.14 mmol) of fluorenyllithium (compound II; prepared as in Example 1a) were dissolved in 250 ml of diethyl ether and, at 0° C., rapidly admixed with 22.40 g (118.18 mmol) of trichloro-β-methallylsilane (compound VII). The mixture was allowed to react at 0° C. for 30 minutes and then stirred at room temperature for three hours, after which most of the solvent was removed by distillation and the LiCl was precipitated using 75 ml of pentane and centrifuged off. The solution was concentrated to half of its original volume and stored at −78° C. The product precipitated as a yellow solid which, on warming to room temperature, melted to give an orange viscous oil. Repeated crystallization from pentane gave 7.1 g (22.24 mmol; 29.6%) of dichlorofluorenyl-β-methallylsilane.

NMR-spectroscopic data
$^1$H-NtMR (C$_6$D$_6$, δ in ppm):

| | |
|---|---|
| 7.77 (d, J = 7.6 Hz) | 4H, aromatic hydrogens on C-1, C-4, C-5, C-8 |
| 7.66 (d, J = 7.6 Hz) | |
| 7.29 ("t", 2H) | 4H, aromatic hydrogens on C-2, C-3, C-6, C-7 |
| 7.23 ("t", 2H) | |

4.57 (s,1H, olefin H in the γ position)

4.31 (s,1H, olefin H in the γ position)

45 3.97 (s,1H, allyl H on C-9)

1.41 (s,2H, methylene hydrogens of the allyl group)

1.41 (s,3H, methyl hydrogens)

$^{13}$C-NMR (C$_6$D$_6$, δ in ppm):

143.4–120.1 (aromatic carbons, olefinic carbons)

113.4 (t, olefinic carbon of the allyl group, J=155.9 Hz)

44.3 (d, C-9)

27.2 (t, methylene carbon of the allyl group, J=122.5 Hz)

24.4 (q, methyl carbon, J=126.1 Hz)

CH analysis: C: calc.: 64.4, found: 67.0; H: calc.: 5.0; found: 5.2 b) Synthesis of 10,10-dichloro-12,12-dimethyl-9,1-(silapropano)fluorene (Compound IX)

2 drops of a 37% HCl solution were added to a suspension of 1.77 g (13.27 mmol) of AlCl$_3$ in 80 ml of benzene. At room temperature, a solution of 4.2 g (13.15 mmol) of compound VIII in 100 ml of benzene was added dropwise with stirring. After the addition had ended, the mixture was stirred for 90 minutes, and 2.03 g (17.45 mmol) of TMEDA were then added to remove the AlCl$_3$. The solution was centrifuged and the benzene was then distilled off under reduced pressure. The brown oily residue was taken up in 80 ml of petroleum ether and crystallized at −25° C. This gave colorless needle-shaped crystals which could be recrystallized from petroleum ether.

Yield: 2.07 g (6.66 mmol; 50.2%; melting point: 113–114° C.).

NMR-spectroscopic data
$^1$H-NMR (C$_6$D$_6$, δ in ppm):

7.69 (m, 2H, aromatic hydrogens)

7.56 (d, 1H, J=7.5 Hz, aromatic hydrogens of positions 4, 5 or 8)

7.25 (m, 3H, aromatic hydrogens)

7.08 (d, 1H, J=7.7 Hz, aromatic hydrogens of positions 4, 5 or 8)

3.95 (s, 1H, allyl H on C-9)

1.21 (AB system, 2H, diastereotopic methylene hydrogens of the six-membered ring, $J_{AAB}$=15.5 Hz; $v_A-v_B$=79.4 Hz)

1.22 (s, 3H, methyl hydrogens)

1.15 (s, 3H, methyl hydrogens)

$^{13}$C-NMR (C$_6$D$_6$, δ in ppm):

| | |
|---|---|
| 144.5 | |
| 142.1 | |
| 141.8 | s, quaternary aromatic carbons |
| 141.4 | |
| 137.9 | |
| 127.5 | |
| 127.0 | |
| 124.8 | doublets of the remaining aromatic carbons |
| 123.0 | |
| 120.8 | |
| 119.0 | |

CH analysis: C: calc.: 64.0; found: 64.5; H: calc.: 5.0; found: 5.4.

c) Reaction of Compound IX with Phenyl-Grignard Reagent (C$_6$H$_5$—MgBr)

2.5 g (7.83 mmol) of the compound IX were dissolved in THF. The phenyl-Grignard reagent, dissolved in THF, was rapidly added with stirring, at room temperature, to the slightly yellowish solution. The color of the reaction mixture immediately changed to orange. The mixture was stirred overnight. The solvent was removed under reduced pressure, giving an orange crystal slurry which was taken up in petroleum ether. This gave a yellow petroleum ether phase which was centrifuged off from a yellow solid insoluble in petroleum ether. The petroleum ether phase was concentrated completely, giving an orange oil.

The insoluble solid was taken up in toluene and heated to about 50° C. This gave a yellow toluene phase which was centrifuged off from a white solid. Removal of the solvent from the toluene phase likewise gave a highly viscous orange oil. This was taken up in hexane and heated to 50° C., giving another yellow hexane phase and an insoluble white powder. After centrifugation and concentration, the hexane phase gave an orange oil.

Both product oils (from the petroleum ether phase and the hexane phase) were combined, giving a total of 1.9 g (5.26 mmol, 67.2%) of compound X.

d) Reaction of Compound X with Tert-butylamine

The 1.9 g (5.26 mmol) of compound X were dissolved in about 20 ml of diethyl ether, and the clear yellow solution was, with stirring, rapidly admixed with 1.1 ml (10.52 mmol) of tert-butylamine. The reaction mixture became milky-turbid. Stirring was continued overnight, and the ether was then removed under reduced pressure. The residue was taken up in petroleum ether, giving, after centrifugation, a yellow solution and a white powder. The petroleum ether phase was concentrated completely, giving 1.8 g (4.53 mmol, 86%) of compound XI as an orange-yellow viscous oil.

e) Synthesis of the Metallocene Complex (Compound XII)

1.8 g (4.53 mmol) of compound XI were dissolved in about 100 ml of ether and stirred. At room temperature, 5.7 ml (9.1 mmol) of n-BuLi were added, and the mixture was stirred overnight. The color of the ether solution, which was originally yellow, changed to a deep red. The ether was removed under reduced pressure, giving an orange foam which was washed with petroleum ether for purification. This gave 750 mg of an orange-yellow powder.

The 750 mg (1.83 mmol) of the dilithium salt of compound XI were dissolved in 100 ml of THF. The dark brown solution was cooled to −78° C. and admixed dropwise with zirconium tetrachloride*2 THF (690 mg, 1.83 mmol) which had been dissolved in 40 ml of THF. The mixture was subsequently stirred at low temperature for two hours and then allowed to warm slowly to room temperature.

The solvent was removed and the dark residue was taken up in toluene and centrifuged. This gave a deep red toluene solution and an insoluble light powder. Concentration of the toluene solution gave an oil which was stirred with petroleum ether for purification. Removal of the wash phase gave 200 mg (0.35 mmol, 19.5%) as a yellow powder.

Example 7

Homopolymerization of Ethylene 25 mg (0.05 mmol) of compound XII were dissolved in 200 ml of toluene and then admixed with 10.9 ml of a 30% strength solution of MAO in toluene (1000 equivalents). The reaction mixture was stirred at room temperature for 30 min, and ethylene was then passed through the solution for 3 h. The reaction was quenched using methanolic HCl and the organic residue was washed with toluene and then dried, giving 0.5 g of polyethylene having a viscosity ($\eta$ value, determined in accordance with ISO 1628-3 at 135° C. in decalin) of 8.95 dl/g.

Example 8

Copolymerization of Ethylene and Hex-1-ene 25 mg (0.05 mmol) of compound XII were dissolved in 200 ml of toluene and then admixed with 10.9 ml of a 30% strength solution of MAO in toluene (1000 equivalents) and with 20 ml of 1-hexene. The reaction mixture was stirred at room temperature for 30 min, and ethylene was then passed through the solution for 6 h. The reaction was quenched using methanolic HCl and the organic residue was washed with toluene and then dried, giving 2.2 g of polyethylene having a viscosity ($\eta$ value, determined in accordance with ISO 1628-3 at 135° C. in decalin) of 8.95 dl/g and a hexene content (determined by IR spectroscopy) of 16.6% by weight.

We claim:

1. A transition metal complex of formula (Ia) or (Ib),

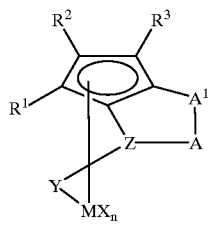
(Ia)

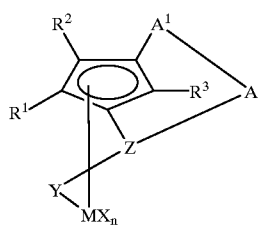
(Ib)

where the substituents and indices have the following meanings:
$R^1$ to $R^3$ are hydrogen, $C_1$–$C_{10}$-alkyl, 5 to 7-membered cycloalkyl, which in turn may be substituted by $C_1$–$C_{10}$-alkyl, are $C_6$–$C_{15}$-aryl or arylalkyl, where the radicals together with adjacent radicals in each case with the linking atoms may form a saturated or unsaturated ring having 5 to 15 carbon atoms, or are $Si(R^4)_3$ where $R^4$ is $C_1$–$C_{10}$-alkyl, $C_3$–$C_{10}$-cycloalkyl or $C_6$–$C_{15}$-aryl, M is titanium, zirconium, hafnium, vanadium, niobium or tantalum or an element of the third group of the Periodic Table or of the lanthanoids, X is fluorine, chlorine, bromine, iodine, hydrogen, $C_1$–$C_{10}$-alkyl, $C_6$–$C_{15}$-aryl, alkylaryl having 1 to 10 carbon atoms in the alkyl radical and 6 to 20 carbon atoms in the aryl radical, —$OR^5$ or —$NR^5R^6$, n is 1, 2 or 3, where n is the valency of M minus the number 2, where
$R^5$ and $R^6$ are $C_1$–$C_{10}$-alkyl, $C_6$–$C_{15}$-aryl, alkylaryl, arylalkyl, fluoroalkyl or fluoroaryl having in each case 1 to 10 carbon atoms in the alkyl radical and 6 to 20 carbon atoms in the aryl radical and the radicals X are identical or different, Y is

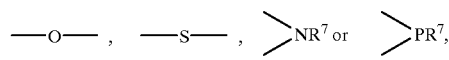

where,
$R^7$ is $C_1$–$C_{10}$-alkyl, $C_6$–$C_{15}$-aryl, $C_3$–$C_{10}$-cycloalkyl or $C_7$–$C_{18}$-alkylaryl or is $C_1$–$C_{10}$-alkyl, $C_6$–$C_{15}$-aryl, $C_3$–$C_{10}$-cycloalkyl or $C_7$–$C_{18}$-alkylaryl, each of which is mono- or polysubstituted by $Si(R^8)_3$, $SR^8OR^8$

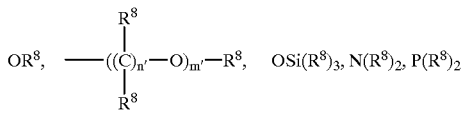

or a combination thereof, or is $Si(R^8)_3$ where n' and m' are each 1, 2, 3 or 4 and
$R^8$ is hydrogen, $C_1$–$C_{10}$-alkyl, $C_6$–$C_{15}$-aryl, which may in turn be substituted by $C_1$–$C_4$-alkyl groups, or is $C_3$–$C_{10}$-cycloalkyl, where the radicals $R^8$ are identical or different, Z is a three-way bridge and A and $A^1$ are two-way bridges.

2. A transition metal complex as claimed in claim 1, in which

Z is

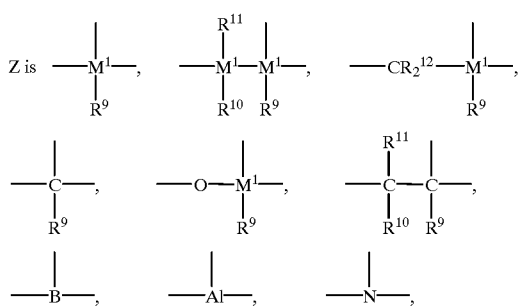

-continued $$-\overset{|}{\underset{}{P}}- \quad \text{or} \quad -\overset{|}{\underset{\overset{\|}{O}}{P}}-,$$

where,

R$^9$ to R$^{12}$ are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group or two radicals R$^9$ to R$^{12}$ together with the linking atoms, form a saturated or unsaturated ring having 4 to 15 carbon atoms, and M$^1$ is silicon, germanium or tin, A is a bridge —(A$^2$)$_m$— where m is from 1 to 6, A$^1$ and A$^2$ are $$-\overset{R^{13}}{\underset{R^{14}}{C}}-, \quad -\overset{R^{13}}{\underset{R^{14}}{Si}}-, \quad -\overset{R^{13}}{\underset{R^{14}}{Ge}}-,$$

$$-\overset{R^{13}}{\underset{R^{14}}{Sn}}-,$$

[aromatic ring structures with R$^{13}$, R$^{14}$, R$^{15}$, R$^{16}$ substituents]

$$=\overset{R^{13}}{C}-, \quad -\overset{R^{13}}{B}-, \quad -\overset{R^{13}}{Al}-, \quad -\overset{R^{13}}{N}-,$$

$$-\overset{R^{13}}{P}-, \quad -\overset{R^{13}}{\underset{\overset{\|}{O}}{P}}-, \quad -\overset{\overset{O}{\|}}{\underset{\overset{\|}{O}}{S}}-,$$

$$-\overset{\overset{O}{\|}}{S}-, \quad -\overset{\overset{O}{\|}}{C}-, \quad -O- \quad \text{or} \quad -S-,$$

where A$^1$ and the individual members A$^2$ or A are identical or different, and R$^{13}$ to R$^{16}$ are identical or different and are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group, or where two adjacent radicals in each case with the linking atoms form a saturated or unsaturated ring having 5 to 15 carbon atoms, or where a radical R$^{13}$ to R$^{16}$ of A$^1$ together with an adjacent radical R$^2$ or R$^3$ form a saturated or unsaturated ring system which has 5 to 15 carbon atoms, including the linking atoms.

3. A transition metal complex as claimed in claim 1, where the transition metal complex (Ia) corresponds to formula (Ia')

(Ia')

[chemical structure showing substituted aromatic ring with R$^1$, R$^2$, R$^{17}$, R$^{18}$, R$^{19}$ substituents, Z, A, Y bridges and MX$_n$]

and

R$^{17}$ to R$^{19}$ are each a hydrogen atom, a C$_1$–C$_{10}$-alkyl group, a 5- to 7-membered cycloalkyl group, which may in turn be substituted by C$_1$–C$_{10}$-alkyl, are a C$_6$–C$_{15}$-aryl group or an arylalkyl group, or where two adjacent radicals in each case with the linking atoms form a saturated or unsaturated ring having 5 to 15 carbon atoms, or are Si(R$^4$)$_3$.

4. A process for preparing the transition metal complex as claimed in claim 1, which comprises reacting cyclopentadiene compounds of formula (IIa) or (IIb), (IIa)

[cyclopentadiene structure with R$^1$, R$^2$, R$^3$, A$^1$X$^1$, X$^2$ substituents]

(IIb)

[cyclopentadiene structure with R$^1$, R$^2$, R$^3$, A$^1$X$^1$, X$^2$ substituents]

in which,

X$^1$ is hydrogen or a halogen and

X$^2$ is hydrogen or a radical of the formula M$^2$R$^{20}$$_{(O-1)}$ in which,

M$^2$ is an element of the 3rd to 6th group of the Periodic Table,

R$^{20}$ is a halogen, a C$_1$–C$_{10}$-alkyl group, a 5- to 7-membered cycloalkyl group, which may in turn be substituted by C$_1$–C$_{10}$-alkyl, is a C$_6$–C$_{15}$-aryl group or an arylalkyl group, where the radicals R$^{20}$ may be identical or different, and O is the valency of M$^2$, with compounds of formula (III), in which (III)

$$\overset{X^4}{\underset{X^3}{\diagdown}}Z-A-X^5$$

$X^3$ and $X^4$ are each a halogen and
$X^5$ is hydrogen, a halogen or a group

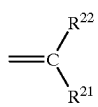

where
$R^{21}$ and $R^{22}$ are each hydrogen, $C_1$–$C_{10}$-alkyl, $C_3$–$C_{10}$-cycloalkyl or $C_6$–$C_{15}$-aryl, to give compounds of formula (IVa) or (IVb), (IVa)
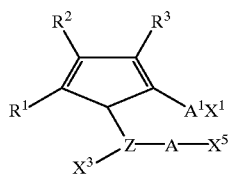

(IVb)
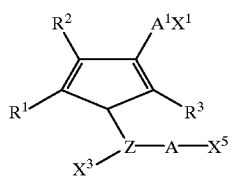

preparing from these by intramolecular ring closure the compounds of formula (Va) or (Vb), (Va)
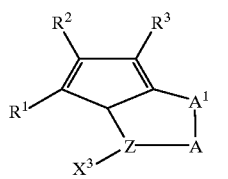

(Vb)
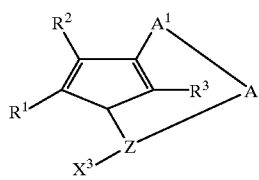

which are converted into compounds of formula (VIa) or (VIb), (VIa)
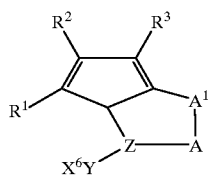

(VIb)
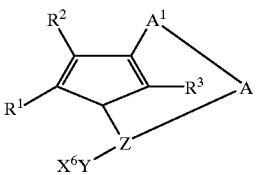

in which
$X^8$ is hydrogen or a radical of the formula $M^3R^{23}{}_{(p-1)}$, in which,
$M^3$ is an element of the 1st–4th main group of the Periodic Table,
$R^{23}$ is a halogen, a $C_1$–$C_{10}$-alkyl group, a 5- to 7-membered cycloalkyl group, which may in turn be substituted by $C_1$–$C_{10}$-alkyl, is a $C_6$–$C_{15}$-aryl group or an arylalkyl group, where the radicals $R^{23}$ may be identical or different, and
p is the valency of $M^3$,
which are then converted into the transition metal complex.

5. A process as claimed in claim 4, wherein, as cyclopentadiene compounds of formula (IIa), indene compounds of formula (IIa'), (IIa')
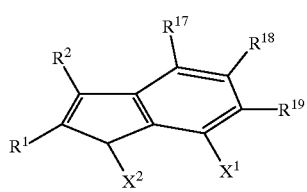

are reacted with a compound of formula (III) to give compounds of formula (IVa'), (IVa')
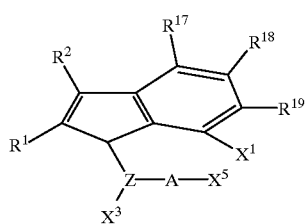

from which, by intramolecular ring closure, the compounds of formula (Va') are prepared (Va')
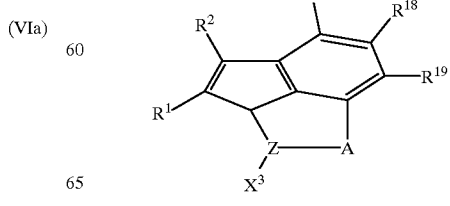

which are reacted to give compounds of formula (VIa')

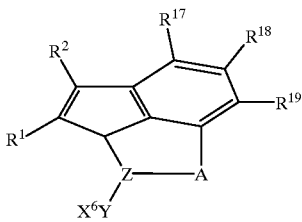

(VIa')

which are then converted into the transition metal complex.

6. A compound of the formula (VIa'),

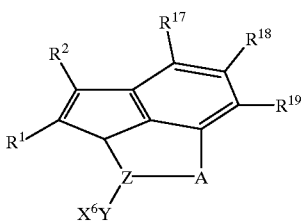

(VIa')

in which the substituents and indices have the following meanings:

$R^1$, $R^2$ and $R^{17}$ to $R^{19}$ are hydrogen, $C_1$–$C_{10}$-alkyl, 5- to 7-membered cycloalkyl, which in turn may be substituted by $C_1$–$C_{10}$-alkyl, are $C_6$–$C_{15}$-aryl or arylalkyl, where two adjacent radicals, in each case with the linking atoms, may form a saturated or unsaturated ring having 5 to 15 carbon atoms, or are $Si(R^4)_3$ where $R^4$ is $C_1$–$C_{10}$-alkyl, $C_3$–$C_{10}$-cycloalkyl or $C_6$–$C_{15}$-aryl, $X^6$ is hydrogen or a radical of the formula $M^3R^{23}{}_{(p-1)}$, in which $M^3$ is an element of the 1st–4th main group of the Periodic Table, $R^{23}$ is a halogen, a $C_1$–$C_{10}$-alkyl group, a 5- to 7-membered cycloalkyl group, which in turn may be substituted by $C_1$–$C_{10}$-alkyl, is a $C_6$–$C_{15}$-aryl group or an arylalkyl group, where the radicals $R^{23}$ may be identical or different, and p is the valency of $M^3$, Y is

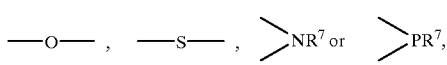

where, $R^7$ is $C_1$–$C_{10}$-alkyl, $C_6$–$C_{15}$-aryl, $C_3$–$C_{10}$-cycloalkyl or $C_7$–$C_{18}$-alkylaryl or is $C_1$–$C_{10}$-alkyl, $C_6$–$C_{15}$-aryl, $C_3$–$C_{10}$-cycloalkyl or $C_7$–$C_{18}$-alkylaryl, each of which is mono- or polysubstituted by $Si(R^8)_3$, $SR^8$, $OR^8$,

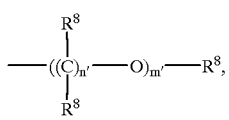

$OR^8$, $OSi(R^8)_3$, $N(R^8)_2$, $P(R^8)_2$ or a combination thereof, or is $Si(R^8)_3$ where n' and m' are each 1, 2, 3 or 4 and $R^8$ is hydrogen, $C_1$–$C_{10}$-alkyl, $C_6$–$C_{15}$-aryl, which may in turn be substituted by $C_1$–$C_4$-alkyl groups, or is $C_3$–$C_{10}$-cycloalkyl, where the radicals $R^8$ are identical or different,

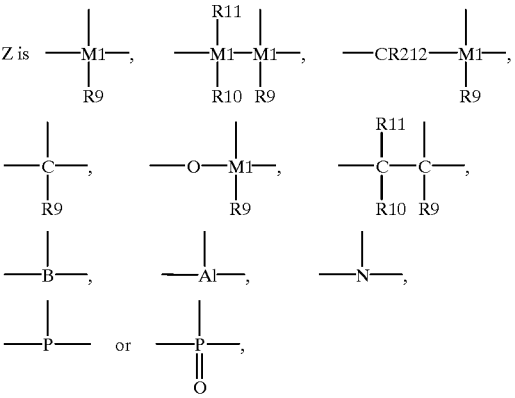

where $R^9$ to $R^{12}$ are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or where two adjacent radicals, in each case with the linking atoms, form a saturated or unsaturated ring having 4 to 15 carbon atoms, and, $M^1$ is silicon, germanium or tin, and A is a bridge —$(A^2)_m$— where m is from 1 to 6, and

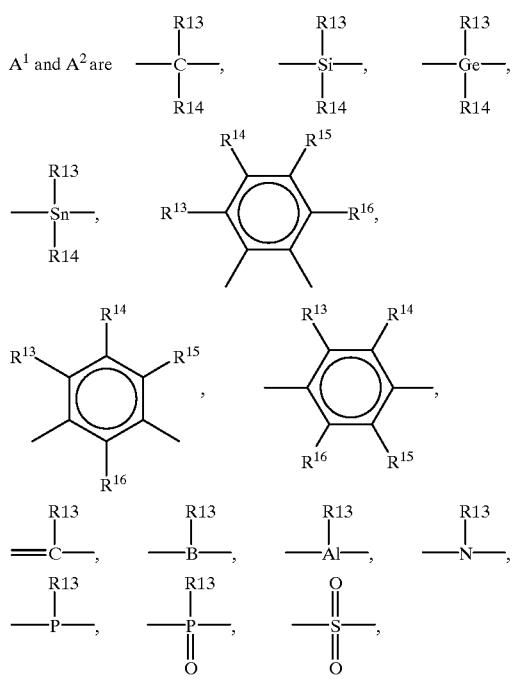

-continued

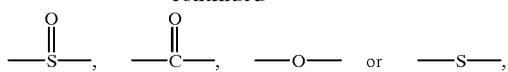

where the individual members $A^2$ or A are identical or different.

7. A compound of formula (IVa'),

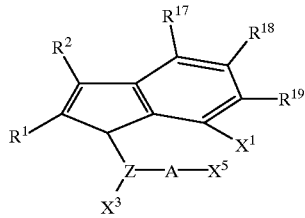

in which the substituents and indices have the following meanings:

$R^1$, $R^2$ and $R^{17}$ to $R^{19}$ are hydrogen, $C_1$–$C_{10}$-alkyl, 5- to 7-membered cycloalkyl, which in turn may be substituted by $C_1$–$C_{10}$-alkyl, $C_6$–$C_{15}$-aryl or arylalkyl, where two adjacent radicals, in each case with the linking atoms, may form a saturated or unsaturated ring having 5 to 15 carbon atoms, or are $Si(R^4)_3$ where $R^4$ is $C_1$–$C_{10}$-alkyl, $C_3$–$C_{10}$-cycloalkyl or $C_6$–$C_{15}$-aryl, $X^1$ is hydrogen or a halogen, $X^3$ is a halogen and $X^5$ is hydrogen, a halogen or a group

where $R^{21}$ and $R^{22}$ are each hydrogen, $C_1$–$C_{10}$-alkyl, $C_3$–$C_{10}$-cycloalkyl or $C_6$–$C_{15}$-aryl,

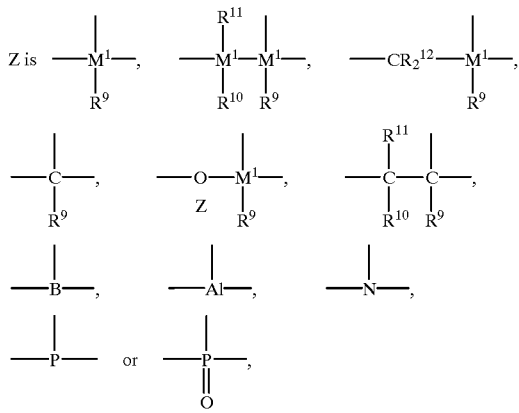

where $R^9$ to $R^{12}$ are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or where two adjacent radicals, in each case with the linking atoms, form a saturated or unsaturated ring having 4 to 15 carbon atoms, and, $M^1$ is silicon, germanium or tin, and A is a bridge —$(A^2)_m$— where m is from 1 to 6, and

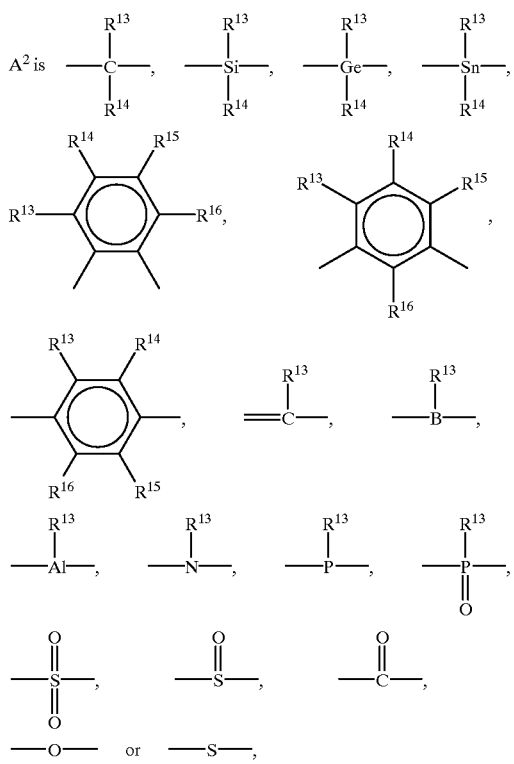

where the individual members $A^2$ of A are identical or different.

8. A process for polymerizing olefins, which comprises carrying out the polymerization in the presence of transition metal complexes as claimed in claim 1 and metallocenium-ion-forming compounds.

9. A homo- or copolymer of ethylene or of propylene with other $C_2$–$C_{12}$-alk-1-enes, obtained by a process as claimed in claim 8.

10. A film, a fiber or a molding comprising homo- or copolymers of ethylene or of propylene with other $C_2$–$C_{12}$-alk-1-enes as claimed in claim 9.

11. A process for polymerizing olefins using a transition metal complex as claimed in claim 1.

12. A process for preparing films, fibers or moldings using a homopolymer or copolymer of ethylene or of propylene with other $C_2$–$C_{12}$-alk-1-enes as claimed in claim 9.

* * * * *

UNITED STATES PATENT AND TRADEMARK OFFICE
CERTIFICATE OF CORRECTION

PATENT NO.    : 6,420,301 B1
DATED         : July 16, 2002
INVENTOR(S)   : Kristen et al.

It is certified that error appears in the above-identified patent and that said Letters Patent is hereby corrected as shown below:

Column 23,
Line 66, "5" should be -- 5- --.

Column 24,
Line 35, "$SR^8OR^8$" should be -- $SR^8$, $OR^8$ --.
Line 40, delete "$OR^8$".

Column 29,
Line 39, "1st-4th" should be -- 3rd through 6th --.

Column 32,
Line 44, "of A" should be -- or A --.

Signed and Sealed this

Fifteenth Day of October, 2002

*Attest:*

JAMES E. ROGAN
*Director of the United States Patent and Trademark Office*

*Attesting Officer*